(12) United States Patent
Mercati et al.

(10) Patent No.: US 10,369,181 B2
(45) Date of Patent: Aug. 6, 2019

(54) DERMO-PROTECTIVE AND DERMO-BALANCING COMPOSITION

(71) Applicant: ABOCA S.P.A. SOCIETA' AGRICOLA, Sansepolcro (IT)

(72) Inventors: Valentino Mercati, Sansepolcro AR (IT); Anna Maidecchi, Sansepolcro AR (IT)

(73) Assignee: ABOCA S.P.A. SOCIETA' AGRICOLA, Sansepolcro AR (IT)

( * ) Notice: Subject to any disclaimer, the term of this patent is extended or adjusted under 35 U.S.C. 154(b) by 773 days.

(21) Appl. No.: 14/389,040

(22) PCT Filed: Mar. 27, 2013

(86) PCT No.: PCT/IB2013/052433
§ 371 (c)(1),
(2) Date: Sep. 29, 2014

(87) PCT Pub. No.: WO2013/144861
PCT Pub. Date: Oct. 3, 2013

(65) Prior Publication Data
US 2015/0064272 A1 Mar. 5, 2015

(30) Foreign Application Priority Data

Mar. 27, 2012 (IT) .............. RM2012A0121

(51) Int. Cl.
| | |
|---|---|
| *A61K 36/23* | (2006.01) |
| *A61K 8/92* | (2006.01) |
| *A61K 8/97* | (2017.01) |
| *A61K 36/38* | (2006.01) |
| *A61Q 19/00* | (2006.01) |
| *A61K 35/644* | (2015.01) |
| *A61K 36/185* | (2006.01) |
| *A61K 36/324* | (2006.01) |
| *A61K 36/328* | (2006.01) |
| *A61L 15/40* | (2006.01) |

(52) U.S. Cl.
CPC .............. *A61K 36/38* (2013.01); *A61K 8/922* (2013.01); *A61K 8/925* (2013.01); *A61K 8/97* (2013.01); *A61K 35/644* (2013.01); *A61K 36/185* (2013.01); *A61K 36/23* (2013.01); *A61K 36/328* (2013.01); *A61L 15/40* (2013.01); *A61Q 19/00* (2013.01); *A61K 36/324* (2013.01)

(58) Field of Classification Search
CPC ...... A61K 36/38; A61K 35/644; A61K 36/23; A61K 36/324
See application file for complete search history.

(56) References Cited

U.S. PATENT DOCUMENTS

| | | | |
|---|---|---|---|
| 5,350,774 A | 9/1994 | Palou | |
| 6,579,543 B1 * | 6/2003 | McClung | ............... A61K 8/345 424/401 |
| 7,744,932 B2 * | 6/2010 | Faller | ..................... A61K 8/347 424/725 |
| 2004/0105873 A1 * | 6/2004 | Gupta | ..................... A61K 8/06 424/401 |
| 2004/0156873 A1 | 8/2004 | Gupta | |
| 2006/0172022 A1 | 8/2006 | Szanzer | |
| 2007/0269537 A1 | 11/2007 | Gupta | |
| 2008/0081034 A1 * | 4/2008 | Zimmerman | ............ A61K 8/35 424/94.1 |
| 2009/0042846 A1 | 2/2009 | Gupta | |
| 2012/0308637 A1 | 12/2012 | Chamberland et al. | |

FOREIGN PATENT DOCUMENTS

| | | | |
|---|---|---|---|
| AU | 630 561 | 10/1992 | |
| CA | 2684258 A1 * | 5/2011 | .......... A61K 36/324 |
| CN | 101 129 678 | 2/2008 | |
| WO | 2011/054090 | 5/2011 | |

OTHER PUBLICATIONS

International Search Report for PCT/IB2013/052433, four pages, dated Jan. 2, 2014.
Written Opinion of the ISA for PCT/IB2013/052433, pages, dated Jan. 2, 2014.
Anonymous "Myrrh" retrieved from www/herbs2000.com/herbs/herbs_myrhh.htm, three pages, Feb. 1, 2012.

* cited by examiner

*Primary Examiner* — Aaron J Kosar
(74) *Attorney, Agent, or Firm* — Sterne, Kessler, Goldstein & Fox P.L.L.C.

(57) ABSTRACT

The treatment of skin lesions and wounds represents one of the eldest problems for humankind and since ancient times remedies have been sought in order to facilitate the repairing of skin tissue with a consequent recovery of a healthy and elastic skin.

21 Claims, 3 Drawing Sheets

DERMO-PROTECTIVE AND DERMO-BALANCING COMPOSITION

This application is the U.S. national phase of International Application No. PCT/IB2013/052433, filed 27 Mar. 2013, which designated the U.S. and claims priority to Italian Application No. RM2012A000121, filed 27 Mar. 2012; the entire contents of each of which are hereby incorporated by reference.

PRIOR ART

The treatment of skin lesions and wounds represents one of the eldest problems for humankind and since ancient times remedies have been sought in order to facilitate the repairing of skin tissue with a consequent recovery of a healthy and elastic skin.

A particular type of lesions is that represented by skin lesions which can also affect underlying tissue and wherein there are no open wounds, such as irritations, rashes, first degree burns, cicatrisation processes of wounds wherein the skin has healed or pressure-caused lesions such as first degree decubitus ulcers. In the case of pressure-caused lesions, such as decubitus ulcers or first degree burns or in the healing process of wounds, ulcers, burns, scars affecting the skin or underlying tissue, it is extremely important to attempt to avoid damages localized in these areas of greater sensitivity.

In these cases it is desirable to treat the skin of the affected region so as to prevent the current condition, even of a minor lesion or partial healing, from worsening, leading to the formation of new lesions.

In the case of pressure-caused lesions, such as for example decubitus ulcers, these are damaged areas located in the skin or underlying tissue caused by pressure, stretching or pressure affecting these areas which is normally due to the patient being unable to move by displacing the areas of pressure in time and, thus, avoid the damages caused by a long absence of microcirculation associated to pressure and rubbing at localized regions.

A decubitus ulcer is a tissue alteration with a necrotic development which affects soft tissues interposed between the support surface and the underlying bone.

Such disease derives from the prolonged decubitus in a fixed position which, by compressing and stretching the tissues, makes them ischemic.

The lesion arises in particularly susceptible places and is favoured by local or general phenomena.

The most affected areas are the sacral, calcaneus and supratrochanteric regions.

In the most serious cases any area underlying a bone surface may be affected.

There are four anatomopathological and clinical "stages" or "types".

Stage or Type I
Persistent erythema with intact skin, is predictive of skin ulcer.

Stage or Type II
Partial thickness skin loss affecting epidermis, derma or both. The ulcer is superficial and appears as an abrasion or thin blister.

Stage or Type III
Full thickness skin loss which involves the damage or necrosis of subcutaneous tissue down to the underlying muscle fascia, without going beyond it. An eschar is initially present, after its removal there remains an ulcer appearing as a deep crater.

Stage or Type IV
Full thickness skin loss, with extensive destruction and necrosis of tissues, muscles, bones and supporting structures (tendons, joint capsules). The lesion is covered by an eschar. After its removal, there remains a deep ulcer which may be undermined and have fistulous paths.

The patient at risk of developing decubitus ulcers shows, as a risk factor, all those conditions where an alteration of mobility in present which implies compression forces, stretching forces and friction forces acting on the skin.

Moreover, in the case of immobility, there exist further known factors which favour the progression of lesions, such as malnutrition, incontinence, cognitive disorder, dehydration, elder age, infections, obesity, excessive thinness, ischemia or hypoxia, etcetera.

Such lesions may be widely prevented and limited via an appropriate medical treatment.

The treatment of decubitus lesions also has considerable social and economic implications, for example the presence of chronic sores (diabetic, venous stasis ulcers, decubitus ulcers, etc.) is very common in human and animal populations (for examples mammalians); the average cost for the treatment of patients is very high and, in the case of human patients, such cost is a considerable burden for national health systems.

In terms of a good medical practice, in order to avoid this type of lesion or to limit the onset thereof, preventive solutions for treating and manipulating the patient are necessary along with an immediate treatment of type I conditions in order to limit as much as possible the progression of the lesion towards stages of a more invasive nature and difficult recovery.

Often, especially when a frequent or prolonged treatment is required, or when subjects who have already undergone various pharmacological treatments are treated or when the conditions of the patient require body positions which do not facilitate tissue regeneration or healing of the skin lesion, it is desirable to use products from a natural source. Consequently, it is preferable to avoid the use of drugs, by using a product of a nonetheless good efficacy for the treatment of lesions wherein the skin and also the underlying tissues may be affected, with no open wounds. Furthermore, in the preventive phase it preferable to not use: ethylic alcohol or alcohol-based products because such substances, in spite of being disinfectant, cause skin dehydration. It is also preferable to avoid the use of very dense pastes which are difficult to remove without using a detergent and powders which reduce the skin's hydrolipidic film.

SUMMARY OF THE INVENTION

The present invention relates to a novel composition for the treatment or prevention of skin lesions which do not involve the presence of open wounds or in the prevention or slowing down of any worsening thereof, comprising, as active ingredients, beeswax, an extract of incense and/or an extract of myrrh; in combination with an extract of *Centella asiatica*, an extract of *Hypericum*, jojoba oil and excipients. Such composition was found, for the selection of the active ingredients, endowed with strong dermo-balancing and dermo-protective action and was found to be of great efficacy in the treatment of elementary or primary skin lesions, that is, those lesions which do not imply the presence of open wounds.

The selection of components described in the present invention was found absolutely nontoxic and well tolerated and made it possible to produce a composition which showed a set of protective, emollient and healing effects effective in the treatment and prevention of skin lesions as well as in the prevention of any potential worsening thereof (for example prevention of the progression from stage I-type decubitus ulcers to stage II-type decubitus ulcers and reversion of type I-decubitus ulcers to healthy skin).

The composition of the invention was found effective, in comparative tests, for the treatment or prevention of skin lesions which do not imply the presence of open wounds and the prevention or slowing down of any worsening thereof with respect to compositions commonly used in these cases, such as for example pomades or creams comprising zinc oxide.

A well-treated skin is less likely to develop lesions and heals more rapidly than a skin in poor conditions, the inventors have created a preventive product capable of maintaining the integrity of the skin's hydrolipidic film, which thanks to its anti-rubbing and anti-friction properties has a barrier effect and consequently indirectly causes the following effects:
  moisturizing/emollient action
  anti-inflammatory lenitive action
  microcirculation-improving action
which are generally desirable actions and particularly useful in cases of incontinence and immobility of the subject to be treated.

DETAILED DESCRIPTION OF THE DRAWINGS

Figure 3:
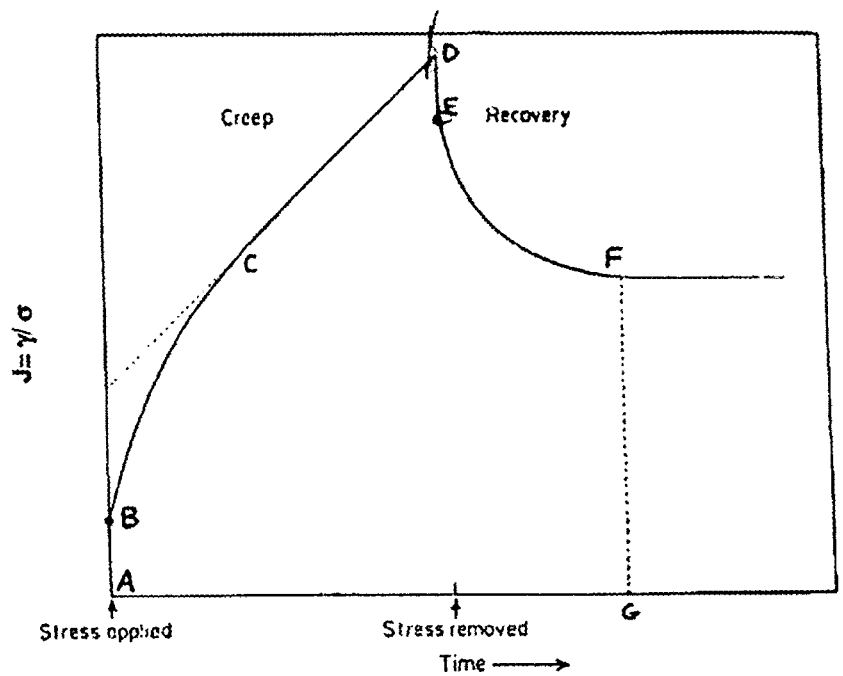

FIG. 3 reports a typical "creep/recovery" profile obtained for a viscoelastic material.

Figure 4:
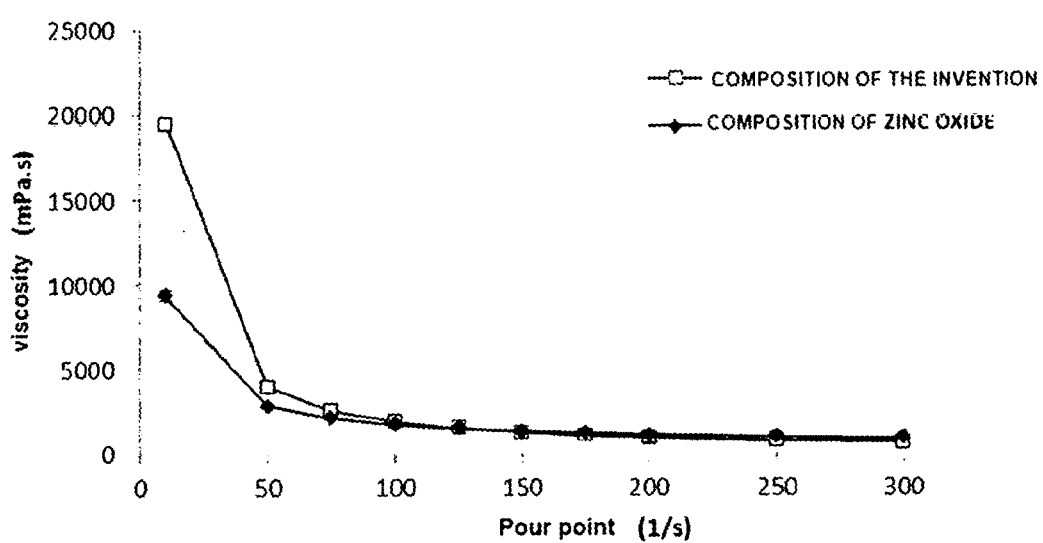

FIG. 4 reports the viscosity profiles of the two formulations being examined.

Both samples are characterised by a pseudoplastic behaviour, that is, by viscosity values which decrease as the applied sliding gradient increases. The degree of pseudoplasticity appears greater for the composition of the invention with respect to the comparison. In the graph the values related to the composition of the invention are reported with white squares and those related to the product with zinc dioxide with black squares.

Figure 5:
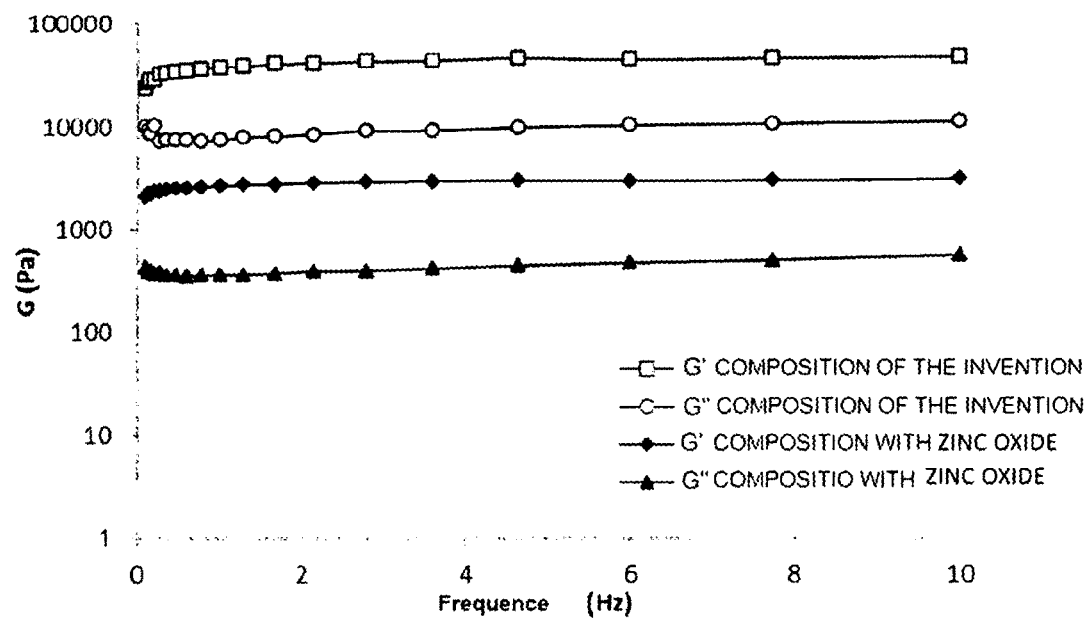

FIG. 5 reports the values of the conservative (G') (white circles for the composition of the invention and black diamonds for the product with zinc oxide) and dissipative (G") (white squares for the composition of the invention and black rectangles for the product with zinc dioxide) moduli obtained for the two formulations being examined as the frequency of application of the shear stress varies, selected in the area of linear viscoelasticity. Values of the conservative (G') and dissipative (G") moduli as a function of the frequency obtained for the two formulations being examined (mean values ±SD; n=3)

Figure 6:
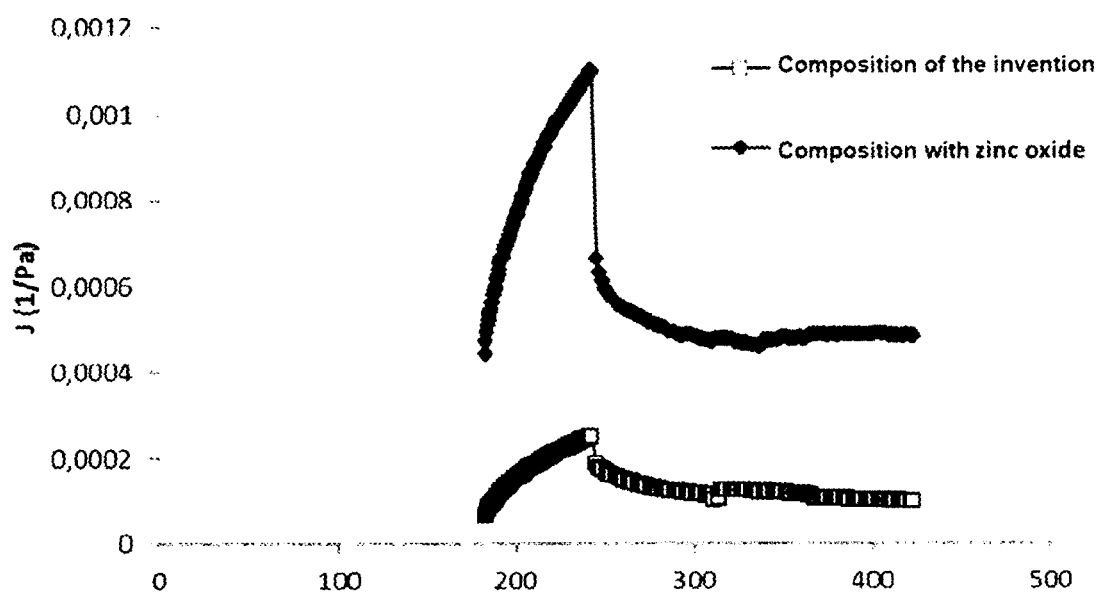

FIG. 6 reports the "creep-recovery" profiles obtained for the two samples being examined. "Creep/recovery" curves obtained for the two samples being examined (mean values ±SD; n=3). Black diamonds product with zinc dioxide, white squares composition of the invention.

DETAILED DISCLOSURE OF INVENTION

The dermo-balancing and dermo-protective composition of the present invention comprises, as main fundamental active components, beeswax, extract of incense and/or extract of myrrh; and extract of *Centella asiatica*, extract of *Hypericum* and jojoba oil. Such composition, thanks to its protecting, emollient and treating effects, has proven particularly effective in the treatment of skin lesions which do not imply the presence of open wounds, in the prevention or slowing down of any progressions to more severe stages of such lesions.

Skin lesions which do not imply the presence of open wounds, according to the present invention, are those lesions wherein the superficial layer of skin and the underlying layers, although not wounded, are particularly fragile, irritated and damaged.

Non-limiting examples of this type of lesions are first degree burns, first degree decubitus ulcers, pressure-caused lesions, rashes, freshly closed wounds or burns, irritations, erythema.

In one embodiment of the invention, the composition described herein is effective in the treatment of pressure-caused lesions such as type I decubitus ulcers by promoting a regression of such stage to non-hyperaemic skin, or slowing down or preventing the progression of type I ulcers to type II ulcers with respect to type I ulcers treated for example with zinc oxide-based compositions, commonly used for this type of treatment.

According to the invention, the composition described herein may also be effective in preventing the onset of rashes due to pathological or non-pathological urinary and faecal incontinence. Such types of incontinence are for example physiological in infants and children up to 2 or 3 years of age and are normally pathological after such age.

In this embodiment the composition described herein may be used for a preventive purpose both as is and incorporated in a device such as a towel, diaper or absorbent pad and the like.

According to the present invention, in accordance with the scientific literature, incense and myrrh are resins of a plant origin secreted physiologically by plants or, more often in response to mechanical trauma (incisions, cuts) or to a stress (pathogen attack) consisting of a complex group of solid, translucent, occasionally liquid, water-insoluble, alcohol-soluble substances, acetone, ether and chloroform.

Such resins contain complex mixtures of alcohols or aliphatic acids, lignans, resin acids, resinotannols, esters and resenes (which derive from polymerization and oxidation processes of essential oil terpenes) and others.

From the chemical point of view many different components are found in resins: alcohols or aliphatic acids having carbonaceous chains of a different length, free aromatic acids, resin acids, monoterpene alcohols, diterpene alcohols, triterpene alcohols, resinols, phenolic compounds of the sterol family, etc.

According to the present invention the composition will comprise incense, myrrh, in a ground (or powdered) form and/or in the form of an extract or mixtures thereof.

The person skilled in the art will in any case be able to identify further resins in addition to those listed herein simply by way of analogy without any use of an inventive step.

The composition may thus contain, as already mentioned, such resins in a powdered, granulated form or in the form of a dry extract and/or lyophilized extract and/or moieties of such extracts which will then be suspended in oil of vegetable and/or mineral origin.

In a particular embodiment the dry component (incense/myrrh grains) will be resuspended to thus form an oily extract, at a percentage from 0.01 to 10% by weight with respect to the oil, in an oil suitable for topic use.

Such oil may be oil of vegetable origin (sunflower seed oil, olive oil, argan seed oil, jojoba oil, sweet almond oil, macadamia nut oil, borage seed oil, *oenothera* seed oil, wheat germ oil, linseed oil) or mineral origin (liquid paraffin) or mixtures thereof.

Advantageously, the extracts of incense and/or myrrh, besides contributing to the creation of a barrier effect on the skin by the composition described herein, also allow the other components of the composition to remain adhering for a longer period in contact with irritated skin, preventing a fast washing away thereof by biological fluids (urines, faeces, sweat), thus allowing the composition to maintain its effect for a longer period and in the most efficient manner.

The oily extract as described herein will be present at a percentage from 40 to 60% by weight of the composition described herein.

This means that the oily extract of incense and/or myrrh may be present in the mixture at a concentration of about 40, 41, 42, 43, 44, 45, 46, 47, 48, 49, 50, 51, 52, 53, 54, 55, 56, 57, 58, 59 or 60% by weight of the composition.

Of course, also decimal numbers between each integer mentioned are included. Such as for example 49.1; 49.2; 49.3; 49.4; 49.5; 49.6; 49.7; 49.8; 49.9 and thus for each integer mentioned for the range above.

The composition will also comprise an extract of *Centella asiatica* (leaves), in a particular embodiment of the invention this may be an oily leaf extract, such extract will be normally present at a concentration by weight of the composition from 10 to 20%, that is about 10, 11, 12, 13, 14, 15, 16, 17, 18, 19, 20% by weight. Also in this case, decimal numbers between each integer mentioned are comprised. By way of example, the total percentage of *Centella asiatica* in the extract described above may be comprised between 0.1 and 10% by weight with respect to the oil.

Of course, also decimal numbers between each integer mentioned are included. Such as for example 15.1; 15.2; 15.3; 15.4; 15.5; 15.6; 15.7; 15.8; 15.9 and thus for each integer mentioned for the range above.

In all the embodiments described herein the "vegetable oils" comprised in the extracts will normally be seed or fruit oils and may be one of the vegetable oils mentioned above or a mixture thereof.

Another active ingredient of the composition according to the invention is represented by an extract of *Hypericum* (flowers and/or leaves and/or peduncle), which may be an oily extract.

Such extract will normally be present at a concentration by weight of the composition from 10 to 20%, that is, about 10, 11, 12, 13, 14, 15, 16, 17, 18, 19, 20% by weight. Also in this case, decimal numbers between each integer mentioned are comprised. By way of example, the total percentage of *Hypericum perforatum* in the extract described above may be comprised between 0.001 and 10% by weight with respect to the oil.

Of course, also decimal numbers between each integer mentioned are included. Such as for example 15.1; 15.2; 15.3; 15.4; 15.5; 15.6; 15.7; 15.8; 15.9 and thus for each integer mentioned for the range above.

The oils may be one or more of the vegetable oils mentioned above.

The composition according to the invention will also comprise jojoba oil, in particular, it may comprise jojoba seed oil. Such oil will be comprised at a concentration by weight of the composition from 5 to 15%, that is, about 5, 6, 7, 8, 9, 10, 11, 12, 13, 14, 15 by weight of the composition. Of course, also decimal numbers between each integer mentioned are included.

Of course, also decimal numbers between each integer mentioned are included. Such as for example 12.1; 12.2; 12.3; 12.4; 12.5; 12.6; 12.7; 12.8; 12.9 and thus for each integer mentioned for the range above.

Finally, the composition will comprise beeswax as an active ingredient at a concentration by weight of the composition from 3 to 17%, that is, about 3, 4, 5, 6, 7% by weight of the composition, comprising the decimal numbers between an integer and the following one.

Of course, also decimal numbers between each integer mentioned are included. Such as for example 5.1; 5.2; 5.3; 5.4; 5.5; 5.6; 5.7; 5.8; 5.9 and thus for each integer mentioned for the range above.

In one embodiment said beeswax is yellow wax from *Apis mellifera* honeycomb.

The disclosure of the present invention reports below some examples of composition wherein the active ingredients are present in the ranges mentioned above.

All the vegetable active ingredients used or the majority thereof will preferably be obtained from organic farming.

In all the cases wherein it has been previously mentioned the use of vegetable oil, such as seed oil, for the preparation of the extracts, such oil may also be in the form of an emulsion oil in water, water in oil or even oil in gel or gel in oil.

Not only may the extracts be in the form of an emulsion, but also the same composition may be formulated as an emulsion. An emulsion "oil in water" is defined as an emulsion wherein the dispersant phase is of the aqueous type and the dispersed phase is of the oily type while the opposite case is an emulsion water in oil.

The composition may further comprise one or more excipients suitable for the creation of a desired final formula which may be for example in the form of an emulsion (also in the form of a cream) oil in water, emulsion water in oil, oil in gel or gel in oil, multiple emulsions, spray and anhydrous formulations (gel, paste, ointment).

Such excipients may be, for example, emulsifiers (cetearyl alcohol, cetearyl glucoside, hydrogenated castor oil), rheological additives, antioxidants (such as vitamins, tocopherols or other antioxidants known in the art).

The emulsifying agent may be a surfactant, which by lowering the interface tension decreases the free energy of the system; in alternative, there may be used non-surfactant substances, such as gum acacia, gelatine or finely separated powders (e.g. talc). In one embodiment the excipients may be present at an overall concentration by weight from 3 to 8%, such concentration obviously being indicative, taking into account that in any case the person skilled in the art will be capable of adapting the concentration of the necessary excipients according to the embodiment they want to prepare without the addition of an inventive step.

The composition may further comprise perfuming and/or colouring agents which give it a pleasant smell, such as for example one or more essential oils such as for example lavender essential oil, *melaleuca* essential oil, lemon, mint, orange and/or colouring agents which allow, for instance, to easily recognize the areas of application of the composition, the colouring being for example temporary so that it does not interfere with other later applications of the composition.

In one embodiment said colouring and/or perfuming agents are comprised at a concentration by weight from 0.001 to 3%.

"Overall concentration by weight" means a concentration by weight in the composition of the total of various excipients or the concentration by weight in the composition of the total of the various perfuming and/or colouring agents present in the composition.

As already mentioned above, the composition of the invention is a composition for topic use which may be designed in the form of an emulsion oil in water, emulsion water in oil, multiple emulsions, creams, sprays and anhydrous formulations (ointment, gel, paste, spray) according to techniques widely used in the art. The formulation herein named "spray" may be an anhydrous formulation or also a formulation in emulsion, the form with spraying dispenser also allowing self-applications in areas which are more difficult to reach (such as for example the back), useful in all those cases wherein the formulation is used, for example, to alleviate sun reddening, erythema or skin irritations of various kinds. Non-limiting examples of the composition according to the invention are as follows.

COMPOSITION EXAMPLE 1

| | |
|---|---|
| Oily extract of incense | from 45 to 55% |
| Oily extract of Centella asiatica | from 12 to 18% |
| Oily extract of Hypericum | from 12 to 18% |
| Jojoba oil | from 7 to 13% |
| Beeswax | from 3 to 7% |
| Trihydroxystearin | from 2 to 6% |
| Tocopherol | from 0.01 to 1.5% |
| Melaleuca essential oil | from 0.01 to 1% |

COMPOSITION EXAMPLE 2

| | |
|---|---|
| Oily extract of myrrh | from 45 to 55% |
| Oily extract of Centella asiatica | from 12 to 18% |
| Oily extract of Hypericum | from 12 to 18% |
| Borage oil | from 2 to 10% |
| Beeswax | from 3 to 7% |
| Colloidal silica | from 2 to 6% |
| Tocopherol | from 0.01 to 1.5% |
| Lavender essential oil | from 0.01 to 2% |

COMPOSITION EXAMPLE 3

| | |
|---|---|
| Oily extract of myrrh | from 5 to 15% |
| Oily extract of Centella asiatica | from 3 to 10% |
| Oily extract of Hypericum | from 3 to 10% |
| Borage oil | from 2 to 10% |
| Beeswax | from 0.5 to 5% |
| Cetylstearyl glucoside | from 2 to 6% |
| Cetylstearyl alcohol | from 2% to 6% |
| Xanthan gum | from 0.2 to 1% |
| Tocopherol | from 0.01 to 1.5% |
| Lavender essential oil | from 0.01 to 2% |
| Melaleuca essential oil | from 0.01% to 0.6% |
| Deionized water | from 40% to 60% |

In Composition example 1, above, percentages of oily extract of incense from 48 and 52%, of oily extract of Centella asiatica from 13 to 16%, of oily extract of Hypericum from 13 to 16%, of beeswax from 4 to 6%, of jojoba oil from 9 to 11% and an overall percentage of excipients from 13 to 0% will be preferred. As mentioned above, all the ranges exemplified above may be substituted by any integer comprised in said ranges (ends included) and by any decimal number between each said integers.

For example, for the particular embodiment of the above-mentioned Composition example 1 48-52% may indicate 48, 49, 50, 51 or 52% and any decimal number comprised between 48 and 49, between 49 and 50, between 50 and 51 and between 51 and 52, such as for example 49.1; 49.2; 49.3; 49.4; 49.5; 49.6; 49.7; 49.8; 49.9 etcetera. Similarly, the range 13-16% may thus indicate 13, 14, 15, or 16% and any decimal number comprised between 13 and 14, between 14 and 15, between 15 and 16, such as for example 12.1; 12.2; 12.3; 12.4; 12.5; 12.6; 12.7; 12.8; 12.9. The range 4-6% may indicate 4, 5, or 6% and any decimal number comprised between 4 and 5 and between 5 and 6, such as for example 5.1; 5.2; 5.3; 5.4; 5.5; 5.6; 5.7; 5.8; 5.9.

The extract of incense or extract of myrrh in the examples above may be substituted by a mixture of extract of incense and of extract of myrrh as described in the present disclosure.

The composition of the invention, when designed in the form of an ointment or emulsion oil in water, or of an oily gel will comprise the extracts described above mainly in the form of oily extracts wherein the only suspending agent may be, for example, represented by a vegetable oil or by a mixture thereof, such as for example sunflower seed oil, linseed oil, jojoba oil, macadamia oil, argan oil, borage seed oil, oenothera seed oil, wheat germ oil or mixtures thereof.

The composition according to the present invention may be designed in the form of a pharmaceutical composition or medical device or comprised in a medical device according to any of the classes described in the 93/42/EEC Directive concerning medical devices (which also comprises substances and not only "devices" in the mechanical sense of the term) or in any form according to the regulatory provisions of the country wherein such composition will be produced.

All the excipients mentioned above will be in a pharmaceutically acceptable form in the case of production of a pharmaceutical composition (therefore, pharmaceutical grade) and may also be so in the case of a medical device.

When present, all the excipients known by the person skilled in the art may be used in the preparation of formulations as mentioned above. A non-limiting example of suitable excipients for the preparation of the composition according to the invention is represented by one or more of Trihydroxystearin (for example Rheocin®), Tocopherol, Melaleuca essential oil, Cetylstearyl glucoside, cetylstearyl alcohol, Xanthan gum, Colloidal silica; lavender essential oil; deionized water; sunflower seed oil, linseed oil, jojoba oil, macadamia oil, argan oil, borage seed oil, oenothera seed oil, wheat germ oil or mixtures thereof.

The excipients may be one or more of the excipients listed above in percentages from 0 to 21%, preferably from 2 to 10%, such as for example about 2, 3, 4, 5, 6, 7, 8, 9, 10%.

Of course, also decimal numbers between each integer mentioned are included. Such as for example 5.1; 5.2; 5.3; 5.4; 5.5; 5.6; 5.7; 5.8; 5.9 and thus for each integer mentioned for the range above.

Most preferred are the compositions wherein the excipient percentage is lower than 6%.

The invention therefore also relates to medical devices such as for example medicated patches, medicated gauzes, medicated bandages, medicated towels, medicated pads, medicated diapers, that is patches, gauzes, bandages, towels, pads or diapers which comprise or are at least partially covered by or are at least partially imbued with the composition of the invention described in the most appropriate form.

The gauzes may be designed as grease gauzes, and similarly the bandages and patches using the composition designed in the form of an ointment, paste or cream for example. The towels may be imbued with the composition in the form of an oil emulsion with water or gel, and the diapers or the absorbent pads may be designed by inserting the composition in the relevant layers known in the art for the insertion of protective or anti-irritating compositions.

Such products such as infant diapers, absorbent pads or common "sanitary pads" for women and adult incontinence pads, are commonly used for example in infancy-, women- and geriatrics-related fields, and the person skilled in the art will know where to insert the composition described herein and which embodiment is the most suitable without the need of particular teachings and only based on the conventional techniques in the art.

Such devices will be applicable to the area to be treated and/or protected for a preventive purpose.

The invention also relates to a method for the treatment or prevention of the onset or worsening of skin lesions which do not imply the presence of open wounds wherein such method comprises one or more applications of the composition of the invention or the medical device which comprises the same once daily or more on the affected area.

The application of the composition, for example, may be repeated whenever needed (for example at each change of diaper in the case of preventing incontinence-related reddening) or one, two, three, for or more times daily in general.

EXAMPLES

1. Skin-Irritation Test Via "Patch Test"

20 healthy volunteers of both sexes between 18 and 60 years of age were recruited. The sample was placed in aluminum Finn Chambers (Bracco) which were applied to the skin of the back and/or to porous patches which were applied to the skin of the forearm. The application of the product to the skin had a duration of 24 hours. Skin reactions were clinically assessed 30 minutes and 24 hours after the removal of the Finn Chamber and 30 minutes and 24 hours after the removal of the porous patch and were interpreted using a system taking into account the severity of the manifestations, according to the scale reported below.

Scale of Skin Reaction Assessment:
0=no erythema;
0.5=minor or unconfirmed erythema;
1=mild spot and diffused redness;
2=moderate and even redness;
3=intense and even redness;
4=burning redness
0=no oedema;
1=very mild oedema (barely visible);
2=mild oedema (well-visible edges);
3=moderate oedema
4=severe oedema (swelling extended beyond the area of application)
Classification of the Mean Irritation Index:
<0.5=non-irritating
0.5-1=slightly irritating
1.0-3=moderately irritating
≥3=severely irritating The composition of the invention was found non-irritating, with a mean irritation index of 0.00 30 minutes after the removal of the patch or chamber and of 0.00 24 hours after the removal of the patch or chamber.

2. Assessment of the Effect of the Composition of the Invention on Patients with Stage I Decubitus Ulcers 50 informed hospitalized patients with type I decubitus ulcers were treated and it was assessed by treating the patients for a period from 3 to 10 days, a week on average.

In these 50 patients, males and females of different age but all suffering from type I decubitus ulcers, treatment with the composition of the invention led to an improvement of the skin conditions and the non-worsening of the same in 94% of analysed cases, and a worsening of the skin situation was observed only in 6% of cases.

In total, the cases in which an improvement in the skin condition was observed were 42%.

In 36% of cases the regression of type I ulcers to non-hyperaemic skin was observed without any doubt.

3. Comparative Test between Treatment with the Composition of the Invention and Treatment with Compositions Comprising Zinc Oxide on Patients with Stage I Decubitus Ulcers The same type of patients analysed previously was assessed by treating a group of patients with the composition according to the invention and with a pomade commonly used for sores, containing zinc oxide and a statistically significant difference was observed (p=0.00235) between the efficacy of the composition of the invention as compared to the efficacy of the zinc oxide pomade. The percentage of subjects showing improvements following treatment with the composition of the invention was 42% (21 subjects) as compared to 20% only (10 subjects) following treatment with zinc oxide. 2% of patients worsened and the rest of them remained stationary.

4. Comparative Barrier Effect Test

As explained in the introductory section of the application, it allows to maintain the integrity of the skin's hydro-lipidic film, indirectly causing the following effects:
moisturizing/emollient action
anti-inflammatory lenitive action
microcirculation-improving action The barrier effect of the composition of the invention also allows the other components of the composition to remain adhering for a longer period in contact with irritated skin, preventing a fast washing away thereof by biological fluids (urines, faeces, sweat), thus allowing the composition to maintain its effect for a longer period and in the most efficient manner.

The barrier effect of the composition as claimed in claim 1 and as exemplified in Composition example 1, and thus comprising as active ingredients an extract of incense and/or of myrrh in combination with an extract of *Centella asiatica*, an extract of *Hypericum*, jojoba oil, beeswax, was thus assessed and the effect of the composition deprived of each of its components was verified.

The data reported below show how the combination of the components selected by the inventors performs an extremely high barrier effect as compared to the composition deprived of any of its components.

The assessment test was carried out as follows through a method developed to simulate in vitro the protective action of substances and formulations which, when applied to the skin and mucous membranes in vivo, form an "insulating" film against environmental agents.

The model takes advantage of the principle whereby cells subjected to contact with an inflammatory agent produce and secrete pro-inflammatory mediators (cytokines) in the extracellular environment in an amount related to the degree of inflammation caused. The greater the amount of inflammatory agent reaching the cells, the greater the amount of cytokines released.

Figure 1:
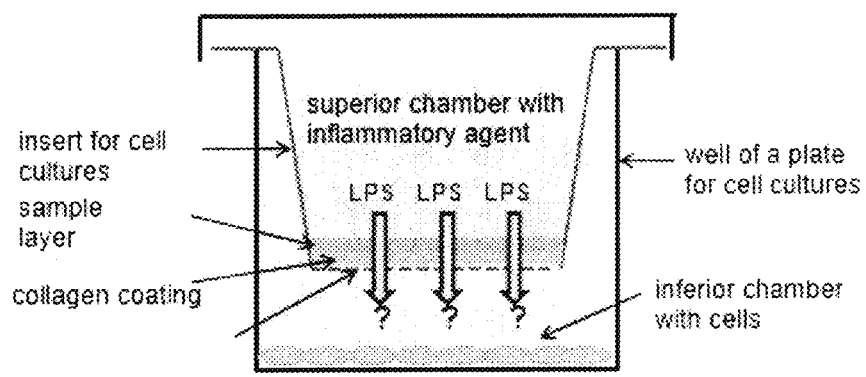
FIG. 1 shows an in vitro experimental model mimicking the conditions of exposure to a barrier product in vivo (Example 4).

The model is provided with the arrangement of two chambers physically separated by a semi-permeable membrane which allows the passage of sufficiently small-sized solutes. [FIG. 1].

In the lower chamber, consisting of a well containing plates for cell cultures, HuDe cells (no. BS PRC 41 bought from the Istituto Profilattico di Brescia, Italy) are grown, while the upper chamber, consisting of an insert for complex cell cultures (transwells), accommodates the inflammatory agent.

On the surface of the semi-permeable membrane of the insert separating the two chambers, before the introduction of the inflammatory agent in the upper chamber, a thin film of the sample being examined is stratified to assess any BE upon the free passage of the inflammatory agent.

As a function of the insulating capabilities of the sample, it will result in a decrease of the migration of the inflammatory agent from the upper chamber and, as a consequence, a lesser stimulation of the cells to produce cytokines. The extent of the inflammatory reaction was calculated through the semi-quantitative dosage of cytokines released in the culture medium of the lower chamber, in particular of interleukin 6 (IL-6).

As a control a similar experiment is used wherein no sample is stratified on the membrane, thus making it possible to measure the effect of the inflammatory agent without any barrier in addition to the semi-permeable membrane.

Further, an internal control is used wherein the cultured cells are pre-treated with the substance adapted to induce the release of the marker and the sample is placed on the semi-permeable membrane in the absence of said substance, one or more measurements in time are thus performed of the quantity of marker in the culture medium of said internal control. In the internal control, the cells are therefore stimulated first with the inducing substance and then there has to be assessed whether the sample which may pass the membrane and go into the cells pushed by the medium above has any effect in decreasing the release of the marker not related to the barrier effect. For example, when an inflammatory agent is used as the inducing substance, the internal control makes it possible to understand if the reduction in the concentration of cytokines in the culture medium is due to the barrier effect or if the sample that may pass into the cells pushed by the medium above has any effect in reducing the inflammatory response independently of the barrier effect.

The barrier effect (BE) is expressed as a percentage of the reduction of the release of IL-6 and is calculated through the comparison with the positive control wherein the two chambers are separated by the same type of semi-permeable membrane without the barrier created by the sample.

4.1 Preparation of the Cell Culture:

For each assayed sample, cells of the HuDe cell line were seeded in the wells of a cell culture plate, one for the barrier test (BT) and another one for the internal control at a density of 40,000 cells/ml in MEM medium supplemented with 10% bovine serum (FBS); 1 ml cell suspension per well.

The cells are treated with the SAMPLE (CAM), with the POSITIVE CONTROL (C+) (inflammatory agent without sample) and with the NEGATIVE CONTROL (C−) (medium only) and each test is carried out in triplicate.

Le plates were incubated at 37° C., overnight (22-24 hours).

4.2 Preparation of Inserts for Complex Cell Cultures

Inserts for complex cell cultures (Becton Dickinson) are placed on other plates (and on each of them a fixed amount of collagen of 0.1 ml/ml is supplied). Le plates were incubated at 37° C., overnight (22-24 hours).

4.3 Verification of State and Level of Cell Confluency

In order to proceed with the experiment, a confluency not lower than 95% is required.

4.4 Collagen Layer Drying

From the two plates (BT and IC) with the inserts the collagen is removed and the insert left under the flow of the hood for the time required to let them dry completely (10-15 minutes).

4.5 Barrier Test (BT)

The steps described below are carried out in the culture plate for the BT

Arrangement of Sample Layer in the BT:

On the sample's semi-permeable membrane 100 µl of a 0.5% alginate composition were inoculated and allowed to stratify for 20 minutes while in the C+ and C− inserts nothing is added. Once the 20 minutes have passed the excess sample is eliminated and the membranes are washed with PBS according to procedures specified by the protocol.

Addition of LPS (Inflammatory Agent) to BT Inserts

Once the sample layer has dried, in the first three CAM inserts and in the three C+ ones, 300 µl of the LPS (membrane lipopolysaccharide) solution were inoculated at the concentration of 1 µg/ml while in the remaining three of the C− 300 µl of MEM medium with 5% FBS were added. The inserts are inserted in their respective wells with the cells and the plates are incubated for 1 h at 37° C. and under an atmosphere enriched with 5% $CO_2$.

Once the 1 h incubation has completed, the inserts are removed and discarded and the plates are incubated again overnight (22-24 hours).

4.6. Internal Control (IC) Test:

The internal control test was carried out at the same time as the BT

Exposure of IC Cells to LPS:

Once dried, in the first six inserts of CI, three for the sample to analyse CAM and three for the C+, 300 µl of the LPS solution are inoculated while in the remaining three of the C− 300 µl of the medium are added.

The inserts with LPS and MEM are then inserted in the wells with IC cells and all incubated for 1 h.

LPS Removal and IC Membrane Drying:

After the 1 h incubation is completed, the inserts are removed from the wells with the cells and transferred to the empty plate while the plate with the cells is placed in an incubator.

The LPS solution still present is removed from the inserts, the latter are subjected to a rapid wash with ultrapure sterile water and allowed to dry.

Arrangement of Sample Layer in the IC:

On the semi-permeable membrane of the three inserts for the sample 100 µl of a 0.5% alginate composition were inoculated and allowed to stratify for 20 minutes while in the C− and C− inserts nothing is added. Once the 20 minutes have passed the excess sample is eliminated and the membranes are washed with PBS according to procedures specified by the protocol.

Addition of LPS to IC Inserts

Once the inserts with the sample are ready, 300 µl of medium are added to all the inserts (CAM, C+, C−). The inserts are inserted in their respective wells with the cells and the plates are incubated for 1 h at 37° C.

Once the 1 h incubation has completed, the inserts are removed and discarded and the plates are incubated again overnight (22-24 hours).

4.7 Supernatant Collection and Enzyme Immunoassay

Once the 22-24 hrs have passed, the supernatants are collected from the BT and the IC plates for performing the ELISA test and semi-quantitative dosage of IL-6.

Barrier Effect (BE) Assessment

The BE of a substance or compound is expressed as a % reduction in the release of IL-6 cytokine by cells exposed to LPS wherein the sample has been tested with respect to the positive control (C+) wherein the cells have only been exposed to LPS.

$$BE = \% \text{ reduction in release of IL-6 cytokine} = 100 - [(pg/\mu L \text{ cytokines released from sample}/pg/\mu L \text{ cytokines released from C+}) \times 100]$$

The data obtained, reported in Table 1 below, show how all the samples assayed (that is, the composition as claimed in claim 1 deprived of one component) were found having, to a lesser or greater extent, a barrier effect.

The results show in particular that the most efficient barrier effect (inhibition of IL-6 cytokine release of 97%) is observed with the composition of the invention with respect to all the other formulations wherein it is absent one of the components of the complete formulation.

TABLE 1

| BARRIER TEST CARRIED OUT ON THE COMPOSITION AS DEFINED IN COMPOSITION EXAMPLE 1 | IL-6 CYTOKINE RELEASE % INHIBITION |
|---|---|
| COMPOSITION COMPRISING AS ACTIVE INGREDIENTS | |
| Oily extract of incense<br>Oily extract of *Centella asiatica*<br>Oily extract of *Hypericum*<br>Jojoba oil<br>Beeswax<br>AS EXCIPIENTS | 97 |
| Trihydroxystearin<br>Tocopherol<br>*Melaleuca* essential oil<br>COMPOSITION COMPRISING AS ACTIVE INGREDIENTS | |
| Oily extract of incense<br>Oily extract of *Centella asiatica*<br>Oily extract of *Hypericum*<br>Jojoba oil<br>AS EXCIPIENTS | 78 |
| Trihydroxystearin<br>Tocopherol<br>*Melaleuca* essential oil<br>(No beeswax)<br>COMPOSITION COMPRISING AS ACTIVE INGREDIENTS | |
| Oily extract of incense<br>Oily extract of *Centella asiatica*<br>Oily extract of *Hypericum*<br>Beeswax<br>AS EXCIPIENTS | 73 |
| Trihydroxystearin<br>Tocopherol<br>*Melaleuca* essential oil<br>(No jojoba oil) | |

TABLE 1-continued

| BARRIER TEST CARRIED OUT ON THE COMPOSITION AS DEFINED IN COMPOSITION EXAMPLE 1 | IL-6 CYTOKINE RELEASE % INHIBITION |
|---|---|
| COMPOSITION COMPRISING AS ACTIVE INGREDIENTS | |
| Oily extract of incense<br>Oily extract of *Hypericum*<br>Jojoba oil<br>Beeswax<br>AS EXCIPIENTS | 51 |
| Trihydroxystearin<br>Tocopherol<br>*Melaleuca* essential oil<br>(No *Centella asiatica*)<br>COMPOSITION COMPRISING AS ACTIVE INGREDIENTS | |
| Oily extract of incense<br>Oily extract of *Centella asiatica*<br>Jojoba oil<br>Beeswax<br>AS EXCIPIENTS | 72 |
| Trihydroxystearin<br>Tocopherol<br>*Melaleuca* essential oil<br>(No *Hypericum*)<br>COMPOSITION COMPRISING AS ACTIVE INGREDIENTS | |
| Oily extract of *Centella asiatica*<br>Oily extract of *Hypericum*<br>Jojoba oil<br>Beeswax<br>AS EXCIPIENTS | 68 |
| Trihydroxystearin<br>Tocopherol<br>*Melaleuca* essential oil<br>(No incense) | |

Similar data were obtained using a composition comprising myrrh instead of incense.

5. Assessment Assay of the Rheological Properties of the Composition of the Invention with Respect to a Product Generally Used for Stage I Decubitus Ulcers The rheological (viscous and viscoelastic) properties of semi-solid formulations, of the composition of the invention were assessed and compared to a commercially available product containing zinc oxide and natural extracts generally used for the purposes described in the present invention.

5.1.1.

The result of the comparative rheological analysis between the composition of the invention carried out according to the detailed Composition example 1 (reported in the detailed disclosure of the invention) is reported below with respect to a commercially available product comprising vegetable extracts and zinc oxide. The comparative product (Bioderm paste) used consists of, in addition to the active ingredient zinc oxide, extract of *Salvia Officinalis*, extract of *Malva Silvestris*, extract of *Chamomilla Recutita*, extract of *Tymus Vulgaris*, beeswax, virgin jojoba oil, sweet almond oil, wheat germ oil, lanoline derivatives, olive oil derivatives, coconut oil derivatives, plant lactic acid, α-Ketoglutaric acid, elastin derivatives, pharmaceutical glycerol, natural moisturizing factors (NMF), hypoallergenic fragrance from vegetable extracts and Bioderm-xiloil® which is a specific silicone-based formulation aggregated with dermocompatible mineral oils.

The rheological properties, as will be described below, are functional to the protective action against external stimuli, shown by such formulations once applied to the skin.

5.1.2 Measurements of Viscosity

The formulations being examined were subjected to viscosity measurements by using a rotational rheometer (Rheostress RS600, Haake, Karlshrue, G) equipped with a plate-cone system (C35/1: Ø=35 mm, angle=1°). The measurements were carried out at the temperature of 37° C., setting increasing sliding gradients in the range 10-300 seconds.

5.1.3 Dynamic Viscoelastic Measurements

The formulations being examined were subjected to dynamic viscoelastic measurements at 37° C., setting a thermostating time of 180 seconds. Such measurements include the application of shear stresses which vary in time in a sinusoidal manner at a certain frequency (1). Differently from what happens in viscosity measurements, in viscoelastic measurements the sample is studied in conditions close to equilibrium, applying very low shear stress values in order to not cause the destruction of its structure.

Stress Sweep Test

Such test is performed in order to investigate for each sample the area of linear viscoelasticity, that is, the range of shear stresses which does not cause variations in the elastic component of the sample (i.e. destruction of its structure).

Figure 2:
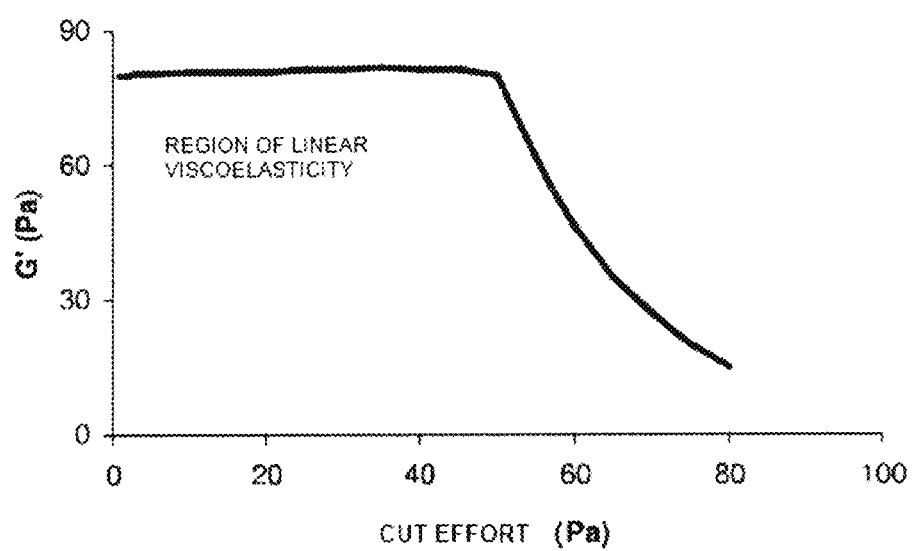
FIG. 2 shows, by way of example, the pattern of the G' modulus in function of the shear stress for a viscoelastic material, the figure represents the typical G' profile obtained by the stress sweep test for a viscoelastic sample.

The samples were subjected to increasing shear stresses at a constant frequency and the pattern of the conservative viscoelastic modulus G' was measured. FIG. 2 reports, by way of example, the pattern of the G' modulus as a function of the shear stress for a viscoelastic material.

The range of shear stresses for which constant values of G' were recorded is defined as linear viscoelasticity area, inside which the shear stress value to be used in the next viscoelastic test (oscillation test) is selected.

Oscillation Test

Such test implies the application of a constant shear stress, selected in the linear viscoelasticity area, at increasing frequencies comprised in the range of 0.1-10 Hz and the measurement of the conservative (G') and dissipative (G") elastic moduli as a function of frequency.

5.1.4 Stationary Viscoelastic Measurements ("Creep-Recovery")

The formulations being examined were subjected to the "creep-recovery" test at 37° C., setting a thermostating time of 180 seconds. Such test implied the application to the sample of a constant shear stress for a certain time and the measurements of the pattern of compliance J (obtained by normalizing the strain suffered from the sample for the shear stress applied) as a function of time ("creep" curve). Once the stress applied is removed, the strain recovered from the sample was measured as a function of time ("recovery" curve) (1).

FIG. 3 reports a typical "creep/recovery" profile obtained for a viscoelastic material.

Generally, in the "creep" curve it is possible to distinguish three different areas (1), detected from portions A-B, B-C and C-D. Portion A-B identifies the region of instant compliance, where the bounds between the structural units of the sample are elastically strained. This area corresponds to the D-E portion in the "recovery" curve which identifies the strain instantly recovered from the sample upon removal of the stress. Portion B-C, to which the EF area corresponds in the "recovery" curve, represents the delayed elastic compliance, that is, the strain recovered non-instantly from the sample, but with a certain delay. Portion C-D, corresponding to the linear region of the "creep" profile, identifies the viscous region which is in relation to the strain no longer recovered from the sample (portion FG). The reciprocal of the slope of the line which interprets the linear portion C-D is in relation to the residual viscosity or $\eta$ which represents the viscosity of the sample in conditions close to rest.

5.2 Measurements of Viscosity

FIG. 4 reports the viscosity profiles of the two formulations being examined.

Both samples are characterised by a pseudoplastic behaviour, that is, by viscosity values which decrease as the applied sliding gradient increases. For sliding gradients greater than 100 1/s the two samples are characterised by two comparable profiles. The degree of pseudoplasticity appears greater for the composition of the invention with respect to the paste containing zinc oxide.

The latter is in fact characterised at low values of the sliding gradient by a lower viscosity as compared to the composition of the invention. This indicates, for the composition of the invention, a greater resistance and thus a greater protection against the application of reduced stresses.

The lowest values of viscosity found for both formulations at high sliding gradients indicate the capability of the two products to dampen the friction forces to a comparable extent.

5.3 Measurements of Viscoelasticity

Both samples showed an area of linear viscoelasticity; it was therefore possible to investigate the viscoelastic properties thereof.

FIG. 5 reports the values of the conservative (G') and dissipative (G") moduli obtained for the two formulations being examined as the frequency of application of the shear stress, selected in the area of linear viscoelasticity, varies.

It may be observed how both samples are characterised by G' values almost independent of frequency, indicating the presence of a "gel-like" structure. Both samples are further characterised by G' values greater than those of G" indicating the prevalence of the elastic behaviour over the viscous one. The composition of the invention is characterised by greater values of both parameters indicating a greater organization of the sample.

FIG. 6 reports the "creep-recovery" profiles obtained for the two samples being examined. It may be observed how the composition of the invention is characterised by a "creep" profile lower than the zinc oxide-containing paste, indicating that the stress applied causes a lower strain in the sample of the invention. In the profile of both samples it is possible to identify the three areas, elastic, delayed elastic and viscous, typical of viscoelastic materials. The composition of the invention has all three strains (elastic, delayed and viscous) lower than the zinc oxide-containing paste. Being the composition of the invention characterised by a slope lower than the last portion of the "creep" curve, it will be characterised by a value of residual viscosity greater than the zinc oxide-containing paste.

5.4. Conclusions

Both samples are characterised by pseudoplastic properties. Such properties are advantageous for the use of products as dermo-protective agents. Low values of viscosity and high sliding gradients guarantee a good spreadability of the product with a greater compliance of the patient. On the other hand, high values of viscosity and low sliding gradients indicate an organization of the sample useful in protecting the area of application when subjected to stresses applied at low speed. In this perspective, the composition of the invention being characterised by a greater degree of pseudoplasticity is endowed with better rheological properties functional to protection.

As regards the results of viscoelastic tests, these show that both samples have a viscoelastic behaviour typical of a "gel-like" structure with an elastic component greater than the viscous one. The elastic properties are functional to the protective action of the products providing a barrier effect against external stresses. The results obtained confirm what was observed at a low sliding value in the viscosity measurements: The composition of the invention is characterised by elastic and viscous components greater than the paste, indicating a greater organization and thus a greater barrier effect.

The invention claimed is:

1. A method for treatment of onset or aggravation of skin lesions that do not involve the presence of open wounds, the method comprising administering an effective amount of a composition comprising the following at a concentration by weight to a subject in need thereof:
   an oily extract of incense from 45% to 55%,
   an oily extract of *Centella asiatica* from 12% to 18%,
   an oily extract of *Hypericum* from 12% to 18%,
   jojoba oil from 7% to 13%,
   beeswax from 3% to 7%, and
   optionally one or more excipients.

2. The method according to claim 1 wherein said skin lesions are sores, first degree burns, pressure-caused lesions, first degree decubitus ulcers, freshly closed wounds or burns, irritations, or rashes.

3. The method according to claim 1, wherein the composition further comprises one or more perfuming and/or colouring agents.

4. The method according to claim 3 wherein said one or more perfuming agents is selected from the group consisting of: lavender essential oil, *melaleuca* essential oil, lemon essential oil, orange essential oil, and mint essential oil.

5. The method according to claim 3 wherein said colouring and/or perfuming agents are comprised at an overall concentration by weight of the composition from 0.05% to 1%.

6. The method according to claim 1 wherein said extract of incense is an extract of incense in oil, oil in water, or oil in gel.

7. The method according to claim 1 wherein said extract of *Centella asiatica* is an extract of leaves in oil, oil in water, or oil in gel.

8. The method according to claim 1 wherein said extract of *Hypericum* is an extract of flowers and/or leaves and/or stalk in oil, oil in water, or oil in gel.

9. The method according to claim 1 wherein said jojoba oil is seed oil.

10. The method according to claim 1 wherein said beeswax is yellow wax from *Apis mellifera* honeycomb.

11. The method according to claim 1 wherein said excipient comprises trihydroxystearin and tocopherol.

12. The method according to claim 1 wherein said oily extract of incense is present in the composition at a weight amount of from 48% to 52%.

13. The method according to claim 1 wherein said oily extract of *Hypericum* is present in the composition at a weight amount of from 13% to 16%.

14. The method according to claim 1 wherein said oily extract of *Centella asiatica* is present in the composition at a weight amount of from 13% to 16%.

15. The method according to claim 1 wherein said jojoba oil is present in the composition at a weight amount of from 9% to 11%.

16. The method according to claim 1 wherein said beeswax is present in the composition at a weight amount of from 4% to 6%.

17. The method according to claim 1 wherein said one or more excipients is comprised at an overall concentration by weight of the composition from 3% to 8%.

18. The method according to claim 1 wherein said composition is in the form of a gel, ointment, cream, pomade, paste, spray, emulsion, suspension, emulsion oil in water, emulsion water in oil, emulsion oil in gel, or emulsion gel in oil.

19. The method according to claim 1 wherein said composition is contained in a medical device that is at least partially covered by or at least partially imbued with the composition.

20. The method according to claim 19 wherein said medical device is in the form of a medicated patch, medicated gauze, medicated bandage, medicated towel, medicated pad, or medicated diaper.

21. A method for providing a barrier effect and/or protecting against an inflammatory agent on skin comprising administering an effective amount of a composition to a subject in need thereof, wherein the composition comprises a concentration by weight of: oily extract of incense from 45% to 55%, oily extract of *Centella asiatica* from 12% to 18%, oily extract of *Hypericum* from 12% to 18%, jojoba oil from 7% to 13%, beeswax from 3% to 7%, and optionally one or more excipients.

* * * * *